(12) United States Patent
Spiecker

(10) Patent No.: US 7,211,807 B2
(45) Date of Patent: May 1, 2007

(54) READOUT METHOD PERFORMED BY STRIPE SCANNING PLANAR OBJECTS WITH SUBSTANCES EMITTING FLUORESCENCE RADIATION

(75) Inventor: Heinrich Spiecker, Bielefeld (DE)

(73) Assignee: LaVision BioTec GmbH, Bielefeld (DE)

( * ) Notice: Subject to any disclaimer, the term of this patent is extended or adjusted under 35 U.S.C. 154(b) by 124 days.

(21) Appl. No.: 11/090,375

(22) Filed: Mar. 25, 2005

(65) Prior Publication Data

US 2005/0211913 A1    Sep. 29, 2005

(30) Foreign Application Priority Data

Mar. 26, 2004  (DE)  ..................... 10 2004 015 488

(51) Int. Cl.
*G01J 1/58*    (2006.01)
(52) U.S. Cl. .................................... 250/459.1
(58) Field of Classification Search .............. 250/459.1
See application file for complete search history.

(56) References Cited

U.S. PATENT DOCUMENTS 5,759,781 A * 6/1998 Ward et al. ..................... 435/6

| | | | |
|---|---|---|---|
| 6,586,750 B2 | 7/2003 | Montagu et al. | |
| 6,613,210 B1* | 9/2003 | Hassard et al. | 204/461 |
| 2002/0036775 A1* | 3/2002 | Wolleschensky et al. | 356/317 |
| 2002/0167662 A1* | 11/2002 | Tanaami et al. | 356/318 |
| 2003/0112432 A1 | 6/2003 | Yguerabide et al. | |
| 2003/0156323 A1* | 8/2003 | Overbeck | 359/385 |
| 2003/0218746 A1 | 11/2003 | Sampas | |
| 2005/0190366 A1* | 9/2005 | Boege et al. | 356/417 |

FOREIGN PATENT DOCUMENTS

| DE | 199 48 391 A1 | 4/2001 |
|---|---|---|
| EP | 1 055 925 A2 | 11/2000 |
| WO | WO 00/43753 | 7/2000 |
| WO | WO 02/06796 A2 | 1/2002 |
| WO | WO 02/39096 A1 | 5/2002 |
| WO | WO 2004/013625 | 2/2004 |

* cited by examiner

*Primary Examiner*—Albert J. Gagliardi
*Assistant Examiner*—Marcus Taningco
(74) *Attorney, Agent, or Firm*—Thomas R. Vigil; Pyle & Piontek

(57) ABSTRACT

The subject matter of the invention is a readout method performed by stripe scanning planar objects with substances emitting fluorescence radiation, a detector being provided and said fluorescence radiation being imaged onto said detector, said detector comprising at least one row of N-linearly disposed single detector segments, with the scanning direction being rotated by angle α with respect to the at least one detector row.

15 Claims, 3 Drawing Sheets

(16) (17) (18)

READOUT METHOD PERFORMED BY STRIPE SCANNING PLANAR OBJECTS WITH SUBSTANCES EMITTING FLUORESCENCE RADIATION

This application claims Priority from German Application No. DE 10 2004 015 488.0 filed on 26 Mar. 2004.

BACKGROUND OF THE INVENTION

1. Field of the Invention

The invention relates to a readout method performed by stripe scanning planar objects with substances emitting fluorescence radiation, a detector being provided and said fluorescence radiation being imaged onto said detector.

2. Description of the Prior Art

A device of the type mentioned herein above is known from EP 2003 076 6413 (WO 2004 013625), said device comprising a UV-source for generating fluorescence radiation, electrically charged substances being read out of a separating medium of a gel electrophoresis apparatus using a detector. The UV detector may hereby be a CCD camera, a photomultiplier, a semiconductor diode or a semiconductor diode array. The readout of larger fields using such a CCD camera is problematic inasmuch as it requires very expensive UV-optics in accordance with the size of the field. Utilizing a photomultiplier is out of the question because the scan duration with such a photomultiplier is much too long. Using semiconductor diodes or a semiconductor diode array is disadvantageous because they are too insensitive.

As already explained above, using a CCD camera to achieve fast readout of such type planar objects is out of the question because, as already discussed, it requires very expensive UV-optics. Provided one would utilize such complicated optics for scanning in order to be able to image quite large areas, scanning would still have to be sequential, meaning that the mechanical device causing either the planar object or the detector to move, must be stopped for each subimage. This places high demands on the mechanics and is moreover time intensive.

Using a photomultiplier, the scanning process is time consuming because the object must be scanned row by row. If a low-cost lamp is for example used as a lighting source, the additional problem arising is that it is not possible to focus enough light onto a sufficiently small spot of the object. As a result, a major part of the light emitted by the lamp must inevitably be eliminated by means of a pinhole.

BRIEF SUMMARY OF THE INVENTION

To speed up the readout process, the present invention proposes that the detector comprises at least one row of N-linearly disposed single detector segments, with the scanning direction being rotated by angle $\alpha$ with respect to the at least one detector row. The object is hereby scanned and read out in overlapping sections by the detector segments of one row. As a result, one row of detector segments generates n-rows of the image. It is important to mention, that the areas of the object corresponding to the individual detector segments are illuminated and the light emitted from those areas is collected simultaneously. It is important to mention, that the areas of the object corresponding to the individual detector segments are illuminated and the light emitted from those areas is collected simultaneously.

If there is a plurality of rows, the angle may be adjusted in such a manner that the image rows scanned by all of the segments are equidistant from one another. This means that, if the detector is rotated by e.g. an angle $\alpha$ with $\tan(\alpha)=1/N$ through a detector having a number N of detector segments along one row, exactly N equidistant lines are viewed by the elements of one row with the N-elements of the next row of the detector again viewing N-lines. All the thus detected lines are equidistant from one another so that, with a detector having N×N elements, N×N lines are captured during one scanning process. The object is stripe scanned and must not be stopped during scanning of a stripe. Beside parallelization and acceleration of the scanning process, this method permits to achieve a high resolution through oversampling. Furthermore, a large portion of the excitation light of a light source may be used if it is not possible to focus on an accordingly small spot.

Advantageous features and developments will become apparent in the subordinate claims.

It is particularly provided that the angle $\alpha$ is determined to $\alpha \geq \frac{1}{16}(\arctan(1/N))$ and more specifically to $\alpha = \arctan(1/N)$. Rotation of the detector rows with respect to the direction of movement of the scanner effects the scanning of the object in overlapping sections. It is known that such a scanning in overlapping sections is beneficial for improving image resolution. To thereby determine the ideal spacing between consecutive lines, the Nyquist sampling theorem may be used.

The Nyquist sampling theorem states that a function $f(y)$—in the case of an object, the curve of the to-be-determined density of the fluorescing substances folded normal to the scan movement (x) with the sensitivity distribution of a detector element along this direction—the spatial frequency spectrum of which lies in the frequency band from 0/mm to B/mm, is clearly determined by its ordinates at equidistant points if these points are not spaced more than ½B mm apart. With sharp imaging, the detector sensitivity is thereby composed multiplicatively of the sample illumination and of the distribution function of the quantum yield of a detector element. To reproduce the original function from the sampled density values, the line spacing must be less than half the reciprocal value of the maximum spatial frequency of the function $f(y)$. By nature, the spatial frequencies of the function $f(y)$ are not substantially higher than 1/row spacing of the detector since by nature the detector segment has approximately the same width as a row. Accordingly, a line spacing of row spacing/2 would be sufficient in this case for a sampling that would tap the full potential of the detector.

There is however the possibility to strongly increase the maximum detectable spatial frequency of the function $f(y)$ either by placing in front of the detector a mask in the form of an aperture diaphragm, said aperture diaphragm reducing the size of the detector segments by masking them or by illuminating the sample in a grid pattern so that each detector segment only collects fluorescence from one point of the object. Such an illumination can be generated using a lens array or an aperture diaphragm. If lasers are used for illumination, beam splitters or holographic elements may be used to divide the light. Aperture diaphragms placed in front of the detector and grid pattern illumination may also be combined with each other. Generally, increasing the maximum detectable spatial frequency in the function $f(y)$ is only advisable in limited instances so that the line spacing needs not be indefinitely small. This again means that a reasonable lower limit for the angle $\alpha$ may be set at approximately $\frac{1}{16}(\arctan(1/N))$. Then, the line spacing in a multiple-row detector is greater than the row spacing/(16×N).

The scanning process itself may be performed by causing the object to move on an x/y-table or by causing the detector to move or by both. It is also possible to place the object onto a cylinder, like a drum scanner. Then, the scanning process may also be performed by carrying out a spiral scanning process through rotation of the cylinder and continuous scanning of the detector along the axis of the cylinder.

The method is particularly suited for scanning separating media of a flatbed electrophoresis apparatus in which the substances are excited to emit native fluorescence. The UV radiation required for this purpose can be advantageously generated by means of a UV lamp. It is well known that it is quite difficult to focus such a lamp since the source spot of the radiation has a volume of about 1 mm$^3$. On the other side, a resolution of about 200 to 500 μm has to be achieved. The method offers the possibility to use almost the full power of the lamp while allowing working with a comparably low-cost detector array.

DETAILED DESCRIPTION OF THE INVENTION

Figure 1:
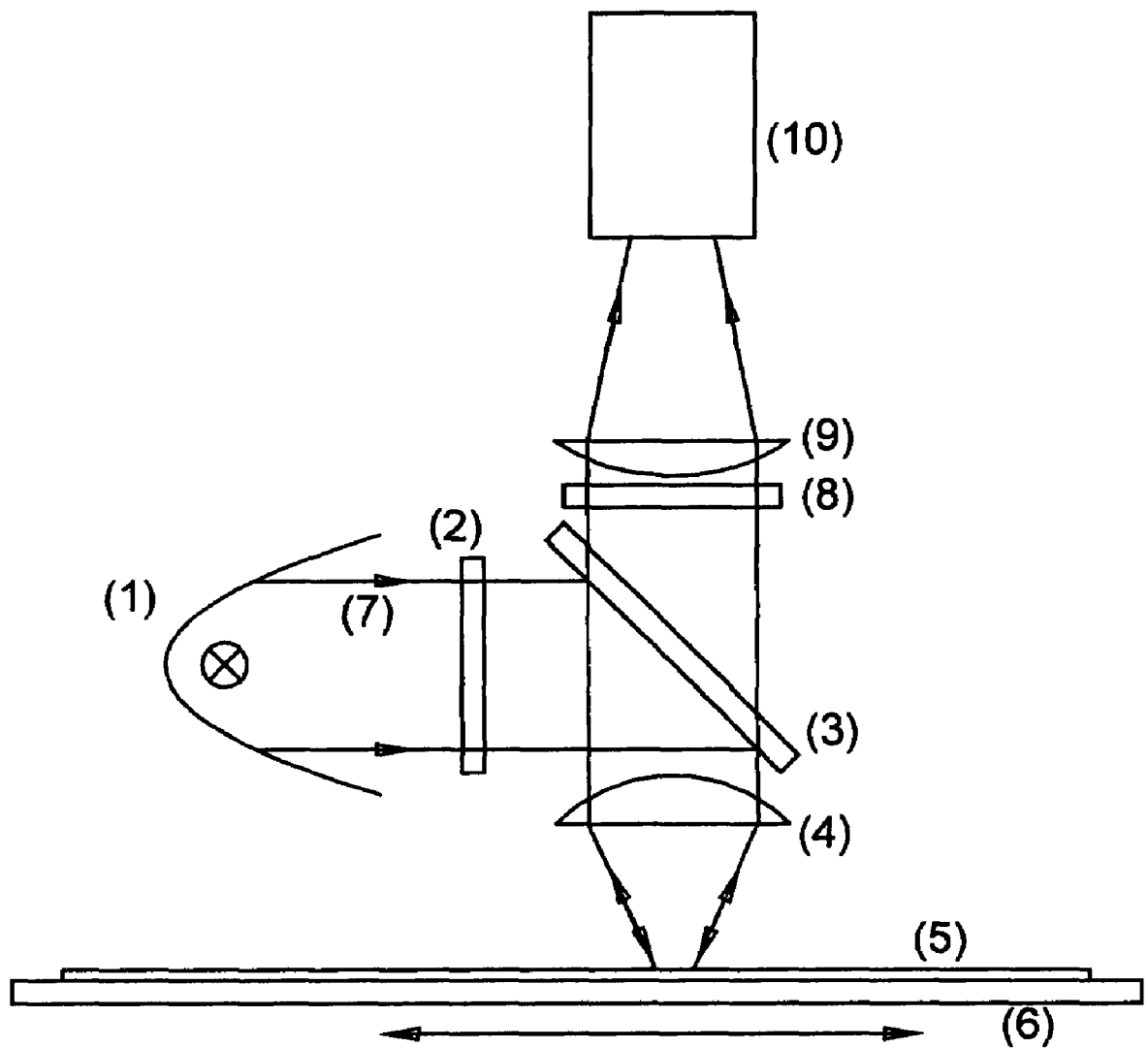
FIG. 1 shows an array for the sampling of a plane object.

FIG. 1 shows, by way of example, an array in which the radiation (7) from a lamp (1) is directed through a filter (2), through a dichroic splitting mirror (3) and an imaging optics (4) onto a sample (5) placed on a movable support (6). The fluorescence light emitted from the sample is then transmitted through the dichroic splitting mirror and imaged by means of a detection filter (8) and optics (9) onto an 8×8 photomultiplier (10).

Figure 2:
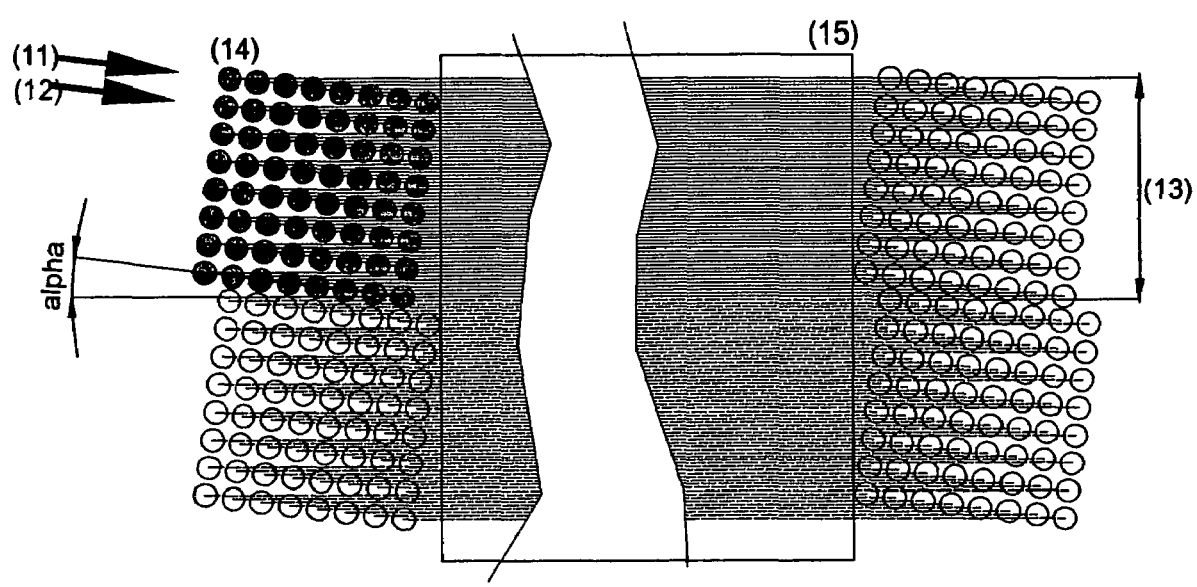
FIG. 2 shows the rotation of the detector.

FIG. 2 shows rotation of the detector rows e.g., (11) and (12) by the angle α of the detector (14) in a direction counter to the scan direction x. At each scanning process, one stripe (13) consisting of 8×8=64 lines is captured. Two scanning operations for generating two stripes are illustrated. Between scanning operations, the sample is displaced in the direction y in such a manner that the resulting lines are equidistant from one another. The to-be-inspected area of the object (15) then lies between the begin point and the end point of the scanning operation.

Figure 3:
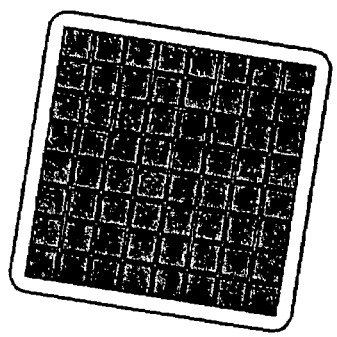
FIG. 3 shows a front view of the detector.
Figure 3:
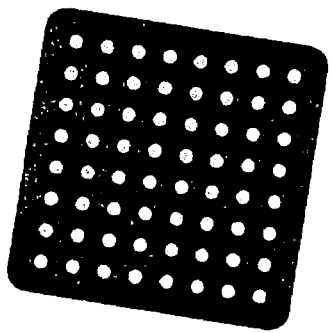
Figure 3:
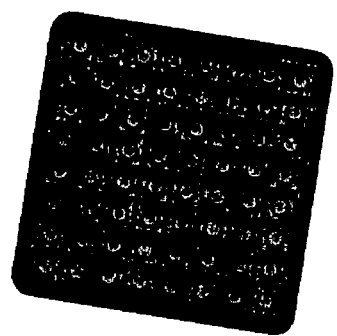

FIG. 3 is a front view showing the 8×8 detector (16) with the detector segments and a possible configuration of a mask (17) as well as its possible position in front of the detector for increasing the resolution (18).

I claim:

1. A readout method performed by stripe scanning planar objects with substances emitting fluorescence radiation, a detector being provided and said fluorescence radiation being imaged onto said detector, said detector comprising more than one row of N-linearly disposed single detector segments, with the scanning direction being rotated by an angle $\alpha \geq \frac{1}{16}$ (arctan1/N) with respect to the at least one detector row where by the areas of the object corresponding to the individual detective segment are illuminated and the light emitted from those areas is collected simultaneously.

2. The method as set forth in claim 1, characterized in that the angle α=arctan (1/N).

3. The method as set forth in claim 1, characterized in that an aperture mask is mounted in front of the detector to increase the resolution.

4. The method as set forth in claim 3, characterized in that a lamp, an LED or a laser is used to generate the fluorescence.

5. The method as set forth in claim 1, characterized in that the excitation wavelength for generating the fluorescence radiation is adaptable to the object to be inspected by using a filter or by selecting the illumination device.

6. The method as set forth in claim 1, characterized in that the detector is configured to be a multianode photomultiplier.

7. The method as set forth in claim 1, characterized in that each detector segment is configured to be a photomultiplier.

8. The method as set forth in claim 1, characterized in that the detector is a CCD camera, a CCD array or a diode array.

9. The method as set forth in claim 1, characterized in that the detector is configured to be UV sensitive.

10. The method as set forth in claim 1, characterized in that the area is configured as a planar or cylindrical shape.

11. The method as set forth in claim 1, characterized in that the object is a separating medium of a flatbed electrophoresis apparatus.

12. The method as set forth in claim 11, characterized in that the separating medium contains substances that are excited with UV light so as to emit native fluorescence radiation.

13. The method as set forth in claim 12, characterized in that the separating medium is selected from the group comprising metal oxides, salts, papers, cellulose or cross-linked, gel-forming polymers.

14. The method as set forth in claim 13, characterized in that the gel-forming polymers are polyacrylamides, agarose or dextran.

15. The method as set forth in claim 1, characterized in that the illumination produced for generating the fluorescence radiation is structured by a mask, a lens array, a holographic element or a beam splitter so that each segment of the detector collects fluorescence radiation from a reduced spot of the object.

* * * * *